(12) United States Patent
Arora

(10) Patent No.: US 7,674,927 B2
(45) Date of Patent: Mar. 9, 2010

(54) FLUORINATED ORGANIC SILICON COATING MATERIAL

(75) Inventor: Pramod K. Arora, North Royalton, OH (US)

(73) Assignee: Innovation Chemical Technologies, Ltd, Cleveland, OH (US)

( * ) Notice: Subject to any disclaimer, the term of this patent is extended or adjusted under 35 U.S.C. 154(b) by 896 days.

(21) Appl. No.: 11/438,813

(22) Filed: May 23, 2006

(65) Prior Publication Data

US 2006/0264650 A1     Nov. 23, 2006

Related U.S. Application Data

(60) Provisional application No. 60/683,624, filed on May 23, 2005.

(51) Int. Cl.
    *C07F 7/04*     (2006.01)
(52) U.S. Cl. ..................................... 556/485
(58) Field of Classification Search .................. 556/485
See application file for complete search history.

(56) References Cited

U.S. PATENT DOCUMENTS

| | | |
|---|---|---|
| 3,038,000 A | 6/1962 | Schmidt |
| 3,950,588 A | 4/1976 | McDougal |
| 5,157,066 A | 10/1992 | Shoji et al. |
| 5,288,889 A | 2/1994 | Takago et al. |
| 5,684,111 A | 11/1997 | Michalczyk et al. |
| 5,763,061 A | 6/1998 | Ochiai et al. |
| 6,183,872 B1 | 2/2001 | Tanaka et al. |
| 6,277,487 B1 | 8/2001 | Soda et al. |
| 6,592,659 B1 | 7/2003 | Terrazas et al. |
| 2003/0027732 A1 | 2/2003 | Howell et al. |

FOREIGN PATENT DOCUMENTS

WO    97/01565    1/1997

OTHER PUBLICATIONS

JP abstract 2001090638, Apr. 3, 2001.*
Howell, et al., New derivatives of poly-hexafluoropropylene oxide from the corresponding alcohol, Journal of Fluorine Chemistry, pp. 281-288, Sep. 2004.
Speier, Homogeneous Catalysts of Hydrosilation by Transition Metals, Advances in Organmetallic Chemistry, vol. 10, pp. 407-447, 1979.
International Search Report for PCT/US06/19843 dated Aug. 31, 2006.

* cited by examiner

*Primary Examiner*—Jafar Parsa
(74) *Attorney, Agent, or Firm*—Turocy & Watson, LLP

(57) ABSTRACT

Disclosed are perfluoropolyether silicon compounds, coatings containing the perfluoropolyether silicon compounds, methods of making the perfluoropolyether silicon compounds, and methods of making perfluoropolyether silicon coatings.

20 Claims, 14 Drawing Sheets

IR Polymer Chain CH2OH amu 2000

IR Polymer Chain CH2OCH2CH=CH2 amu 2000

Polymer Chain-$CH_2OCH_2CH=CH_2$ amu 2000 NMR

Polymer chain-SiCl₃ 2000 amu   IR

NMR Polymer Chain-SiCl$_3$ amu 2000

IR Polymer Chain-SiCl$_3$ amu 4000

NMR Polymer Chain-SiCl$_3$ amu 4000

IR Polymer Chain-Si(OMe)₃ amu 4000

Polymer Chain-$CH_2OCH_2CH=CH_2$ amu 4000 IR

FLUORINATED ORGANIC SILICON COATING MATERIAL

RELATED APPLICATION

This application claims priority to U.S. Provisional Patent Application 60/683,624 filed on May 23, 2005, which is hereby incorporated by reference.

TECHNICAL FIELD

The subject invention generally relates to perfluoropolyether silicon compounds, coatings containing the perfluoropolyether silicon compounds, methods of making the perfluoropolyether silicon compounds, and methods of making perfluoropolyether silicon coatings.

BACKGROUND

Polymerizable amphiphilic molecules and hydrolysable alkyl silanes are employed to form thin films on various surfaces. Thin films have numerous and diverse useful purposes. For example, a thin film may be formed on a lens for scratch resistance or on a metal for corrosion protection.

Oil repellent coatings and water repellent coatings may be provided to certain substrates by applying to a substrate fluorinated silanes. The applied fluorinated silanes are often cured by heating with a catalyst to chemically affix the fluorinated silanes to the substrates. In some instances, durability of the oil repellent coatings and water repellent coatings is an issue.

One problem with applying fluorinated silanes to substrates is that the fluorinated silanes may not have a long shelf live. Another problem is that fluorinated silanes often require high-shear mixing before coating on a substrate. Many fluorinated silane compositions have a high solids content, which results in thick coatings. This can be a problem when thin coatings are desired.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter.

The subject invention provides perfluoropolyether silicon compounds, convenient and simple methods of making the perfluoropolyether silicon compounds, hydrophobic coatings containing the perfluoropolyether silicon compounds, and efficient methods of making perfluoropolyether silicon coatings.

To the accomplishment of the foregoing and related ends, the invention comprises the features hereinafter fully described and particularly pointed out in the claims. The following description and the annexed drawings set forth in detail certain illustrative aspects and implementations of the invention. These are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION

Figure 1:
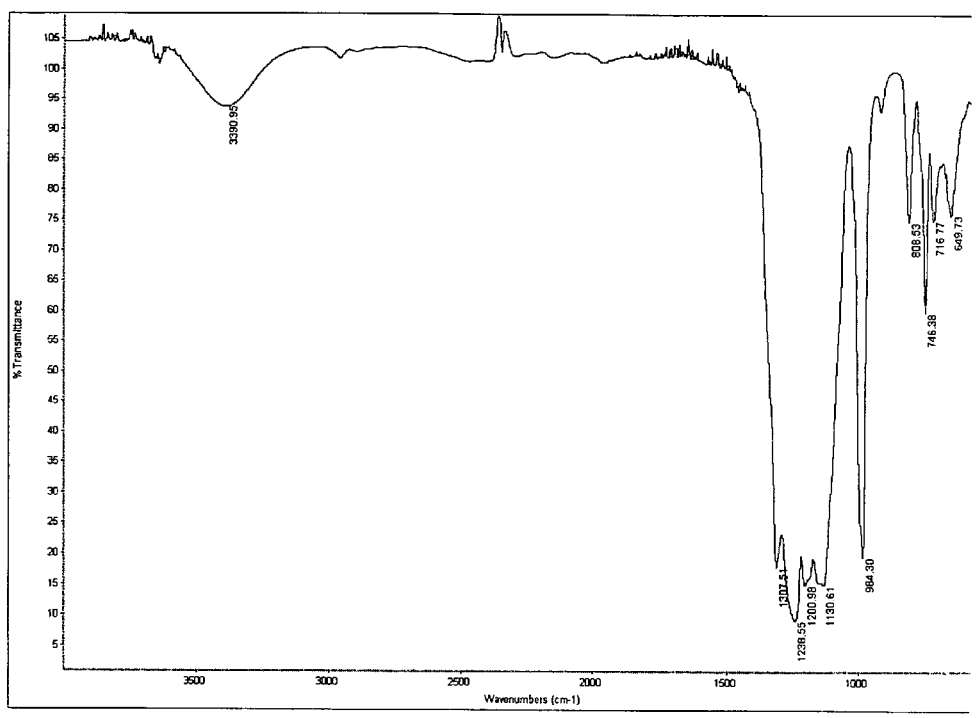
FIG. 1 is an IR spectrum of an alcohol perfluoroether in accordance with an aspect of the invention.

One end of a perfluoroether that is branched or unbranched is functionalized, then reacted with a hydrocarbon containing compound such as an allyl compound, then subject to hydrosilation with a silane to form a perfluoropolyether silicon compound. The perfluoropolyether silicon compound can be employed as a glass coating, such as an anti-scratch coating for eyeglasses.

In one embodiment, the perfluoropolyether silicon compounds are represented by Formula I:

$$R_m SiH_n R^2 OCH_2 Z \qquad (I)$$

where each R is independently an alkyl, hydroxyalkyl, alkoxy, alkyl ether, aryl, aryloxy, substituted aryl, all of which contain from about 1 to about 20 carbon atoms, halogens, hydroxy, and acetoxy; $R^2$ is alkyl containing from about 2 to about 10 carbon atoms; Z is fluorinated alkyl ether containing from about 2 to about 2,000 carbon atoms; and m is from about 1 to about 3, n is from 0 to about 2, and m+n equal 3. Halogens include fluorine, chlorine, bromine and iodine. In another embodiment, each R is independently an alkyl, hydroxyalkyl, alkoxy, all of which contain from about 2 to about 10 carbon atoms; $R^2$ is alkyl containing from about 2 to about 5 carbon atoms; Z is fluorinated alkyl ether containing from about 5 to about 1,500 carbon atoms; and m is from about 2 to about 3, n is from 0 to about 1, and m+n equal 3. The fluorinated alkyl ether may be branched or unbranched. Dimer compounds of Formula I are also possible perfluoropolyether silicon compounds $(R_mSiH_nR^2OCH_2ZCH_2OR^2SiH_nR_m)$.

In another embodiment, the perfluoropolyether silicon compounds are represented by Formula IIa:

$$R_3SiCH_2CH_2CH_2OCH_2Z \quad \text{(IIa)}$$

where each R is independently an alkyl, hydroxyalkyl, alkoxy, alkyl ether, aryl, aryloxy, substituted aryl, all of which contain from about 1 to about 20 carbon atoms, halogens, hydroxy, and acetoxy; Z is fluorinated alkyl ether containing from about 2 to about 2,000 carbon atoms. In another embodiment, each R is independently an alkyl, hydroxyalkyl, alkoxy, all of which contain from about 2 to about 10 carbon atoms; and Z is fluorinated alkyl ether containing from about 10 to about 1,500 carbon atoms. The fluorinated alkyl ether may be branched or unbranched. The perfluoropolyether silicon compounds may also be dimer compounds of Formula IIa, such as those represented by Formula IIb:

$$R_3SiCH_2CH_2CH_2OCH_2ZCH_2OCH_2CH_2CH_2SiR_3 \quad \text{(IIb)}$$

where each R is independently an alkyl, hydroxyalkyl, alkoxy, alkyl ether, aryl, aryloxy, substituted aryl, all of which contain from about 1 to about 20 carbon atoms, halogens, hydroxy, and acetoxy; Z is fluorinated alkyl ether containing from about 2 to about 2,000 carbon atoms. In another embodiment, each R is independently an alkyl, hydroxyalkyl, alkoxy, all of which contain from about 2 to about 10 carbon atoms; and Z is fluorinated alkyl ether containing from about 5 to about 1,500 carbon atoms. The fluorinated alkyl ether may be branched or unbranched.

The fluorinated alkyl ether portion of the perfluoropolyether silicon compounds, often the "Z" portion in the equations above, contain repeating fluorocarbon ether units. Since too many examples exist to list each, exemplary examples include:

$$-\!\!\!-\!\![(CF_2)_nO]_mR^1 \quad \text{(III)}$$

$$-\!\!\!-\!\![(CF_2)_p(CF)_qO]_mR^1 \quad \text{(IV)}$$
$$\phantom{xxxxxx}|$$
$$\phantom{xxxxxx}R^1$$

$$-\!\!\!-\!\![(CF)_q(CF_2)_pO]_mR^1 \quad \text{(V)}$$
$$\phantom{xxxxxx}|$$
$$\phantom{xxxxxx}R^1$$

$$-\!\!\!-\!\![(CF_2)_pO(CF)_q]_mR^1 \quad \text{(VI)}$$
$$\phantom{xxxxxx}|$$
$$\phantom{xxxxxx}R_1$$

$$-\!\!\!-\!\![(CF)_qO(CF_2)_p]_mR^1 \quad \text{(VII)}$$
$$\phantom{xxxxxx}|$$
$$\phantom{xxxxxx}R^1$$

$$-\!\!\!-\!\![(CF_2)_p(CF)_qO]_m[(CF_2)_nO]_mR^1 \quad \text{(VIII)}$$
$$\phantom{xxxxxx}|$$
$$\phantom{xxxxxx}R^1$$

$$-\!\!\!-\!\![(CF)_q(CF_2)_pO]_m[(CF_2)_nO]_mR^1 \quad \text{(IX)}$$
$$\phantom{xxxxxx}|$$
$$\phantom{xxxxxx}R^1$$

$$-\!\!\!-\!\![(CF_2)_pO(CF)_q]_m[(CF_2)_nO]_mR^1 \quad \text{(X)}$$
$$\phantom{xxxxxx}|$$
$$\phantom{xxxxxx}R^1$$

$$-\!\!\!-\!\![(CF)_qO(CF_2)_p]_m[(CF_2)_nO]_mR^1 \quad \text{(XI)}$$
$$\phantom{xxxxxx}|$$
$$\phantom{xxxxxx}R^1$$

-continued $$-\!\!\!-\!\![(CF_2)_p(CF)_qO]_m[(CF_2)_nO]_m[(CF)_q(CF_2)_pO]_mR^1 \quad \text{(XII)}$$
$$\phantom{xxxxxx}|\phantom{xxxxxxxxxxxxxxxxxx}|$$
$$\phantom{xxxxxx}R^1\phantom{xxxxxxxxxxxxxxxxxx}R^1$$

$$-\!\!\!-\!\![(CF_2)_pO(CF)_q]_m[(CF_2)_nO]_m[(CF)_qO(CF_2)_p]_mR^1 \quad \text{(XIII)}$$
$$\phantom{xxxxxx}|\phantom{xxxxxxxxxxxxxxxxxx}|$$
$$\phantom{xxxxxx}R^1\phantom{xxxxxxxxxxxxxxxxxx}R^1$$

wherein each $R^1$ is independently any of $CF_3$, $C_2F_5$, $C_3F_7$, $CF(CF_3)_2$, and similar groups such as similar fluoro-carbon groups and fluoro-hydrocarbon groups; each m is independently from about 2 to about 300; each n is independently from about 1 to about 5; each p is independently from about 0 to about 5; and each q is independently from about 0 to about 5. In another embodiment, each m is independently from about 5 to about 100; each n is independently from about 2 to about 4; each p is independently from about 1 to about 4; and each q is independently from about 1 to about 4. In any of the formulae above, occasional substitution of a fluorine atom with a hydrogen atom that does not affect the overall perfluoro nature of the fluorinated alkyl ether portion is acceptable.

In one embodiment, the perfluoropolyether silicon compounds do not contain an amide moiety (—CONH—) within the perfluoropolyether ligand of the silicon atom. Since an amide moiety with the perfluoropolyether ligand of the silicon atom may, in many instances, lead to a compound with thermal instability, the perfluoropolyether silicon compounds of the invention have excellent high temperature stability.

Generally speaking, the perfluoropolyether silicon compounds can be made by hydrosilating a hydrocarbylized perfluoroether. An example of a hydrocarbylized perfluoroether is a KRYTOX allyl ether available from DuPont. Alternatively, the perfluoropolyether silicon compounds can be made by hydrocarbylating a functionalized perfluoropolyether to provide a hydrocarbylized perfluoroether, which is then subject to hydrosilation to form the perfluoropolyether silicon compound.

The perfluoroethers that are functionalized, then reacted with a hydrocarbon containing compound such as an allyl compound, are the corresponding compounds of the fluorinated alkyl ether portions described above. For example, in the case of the fluorinated alkyl ether in Formulae (III)-(VIII), the perfluoroether starting material may be one or more of any of compounds represented by Formulae (XIV-III) to (XIX-VIII):

$$FOC[(CF_2)_nO]_mR^1 \quad \text{(XIV-III)}$$

$$R^2O_2C[(CF_2)_nO]_mR^1 \quad \text{(XV-III)}$$

$$R^2O[(CF_2)_nO]_mR^1 \quad \text{(XVI-III)}$$

$$HO_2C[(CF_2)_nO]_mR^1 \quad \text{(XVII-III)}$$

$$FO[(CF_2)_nO]_mR^1 \quad \text{(XVIII-III)}$$

$$HOH_2C[(CF_2)_nO]_mR^1 \quad \text{(XIX-III)}$$

$$FOC[(CF_2)_p(CF)_qO]_mR^1 \quad \text{(XIV-IV)}$$
$$\phantom{xxxxxxxx}|$$
$$\phantom{xxxxxxxx}R^1$$

$R^2O_2C[(CF_2)_p(CF)_qO]_mR^1$ (XIV-IV)
|
$R^1$ $R^2O[(CF_2)_p(CF)_qO]_mR^1$ (XV-IV)
\
$R^1$ $HO_2C[(CF_2)_p(CF)_qO]_mR^1$ (XVI-IV)
|
$R^1$ $FO[(CF_2)_p(CF)_qO]_mR^1$ (XVII-IV)
|
$R^1$ $HOH_2C[(CF_2)_p(CF)_qO]_mR^1$ (XVIII-IV)
|
$R^1$ $FOC[(CF)_q(CF_2)_pO]_mR^1$ (XIX-IV)
|
$R^1$ $R^2O_2C[(CF)_q(CF_2)_pO]_mR^1$ (XIV-V)
|
$R^1$ $R^2O[(CF)_q(CF_2)_pO]_mR^1$ (XV-V)
\
$R^1$ $HO_2C[(CF)_q(CF_2)_pO]_mR^1$ (XVI-V)
|
$R^1$ $FO[(CF)_q(CF_2)_pO]_mR^1$ (XVII-V)
\
$R^1$ $HOH_2C[(CF)_q(CF_2)_pO]_mR^1$ (XVIII-V)
|
$R^1$ $FOC[(CF_2)_pO(CF)_q]_mR^1$ (XIX-V)
|
$R^1$ $R^2O_2C[(CF_2)_pO(CF)_q]_mR^1$ (XIV-VI)
|
$R^1$ $R^2O[(CF_2)_pO(CF)_q]_mR^1$ (XV-VI)
|
$R^1$ $HO_2C[(CF_2)_pO(CF)_q]_mR^1$ (XVI-VI)
|
$R^1$ $FO[(CF_2)_pO(CF_2)_q]_mR^1$ (XVII-VI)
\
$R^1$ $HOH_2C[(CF_2)_pO(CF)_q]_mR^1$ (XVIII-VI)
|
$R^1$ $FOC[(CF)_qO(CF_2)_p]_mR^1$ (XIX-VI)
|
$R^1$ $R^2O_2C[(CF)_qO(CF_2)_p]_mR^1$ (XIV-VII)
|
$R^1$ $R^2O[(CF)_qO(CF_2)_p]_mR^1$ (XV-VII)
\
$R^1$ $HO_2C[(CF)_qO(CF_2)_p]_mR^1$ (XVI-VII)
|
$R^1$ $FO[(CF)_qO(CF_2)_p]_mR^1$ (XVII-VII)
|
$R^1$ $HOH_2C[(CF)_qO(CF_2)_p]_mR^1$ (XVIII-VII)
|
$R^1$ $FOC[(CF_2)_p(CF)_qO]_m[(CF_2)_nO]_mR^1$ (XIX-VII)
|
$R^1$ $R^2O_2C[(CF_2)_p(CF)_qO]_m[(CF_2)_nO]_mR_1$ (XIV-VIII)
|
$R^1$ $R^2O[(CF_2)_p(CF)_qO]_m[(CF_2)_nO]_mR_1$ (XV-VIII)
\
$R^1$ $HO_2C[(CF_2)_p(CF)_qO]_m[(CF_2)_nO]_mR^1$ (XVI-VIII)
|
$R^1$ $FO[(CF_2)_p(CF)_qO]_m[(CF_2)_nO]_mR^1$ (XVII-VIII)
|
$R^1$ $HOH_2C[(CF_2)_p(CF)_qO]_m[(CF_2)_nO]_mR^1$ (XVIII-VIII)
|
$R^1$ $FOC[(CF)_q(CF_2)_pO]_m[(CF_2)_nO]_mR^1$ (XIX-VIII)
|
$R^1$ $R^2O_2C[(CF)_q(CF_2)_pO]_m[(CF_2)_nO]_mR^1$ (XIV-IX)
|
$R^1$ $R^2O[(CF)_q(CF_2)_pO]_m[(CF_2)_nO]_mR^1$ (XV-IX)
|
$R^1$ $HO_2C[(CF)_q(CF_2)_pO]_m[(CF_2)_nO]_mR^1$ (XVI-IX)
|
$R^1$ $FO[(CF)_q(CF_2)_pO]_m[(CF_2)_nO]_mR^1$ (XVII-IX)
|
$R^1$ $HOH_2C[(CF)_q(CF_2)_pO]_m[(CF_2)_nO]_mR^1$ (XVIII-IX)
|
$R^1$ $FOC[(CF_2)_pO(CF)_q]_m[(CF_2)_nO]_mR^1$ (XIX-IX)
|
$R^1$ $R^2O_2C[(CF_2)_pO(CF)_q]_m[(CF_2)_nO]_mR^1$ (XIV-X)
|
$R^1$ $R^2O[(CF_2)_pO(CF)_q]_m[(CF_2)_nO]_mR^1$ (XV-X)
|
$R^1$ (XVI-X)

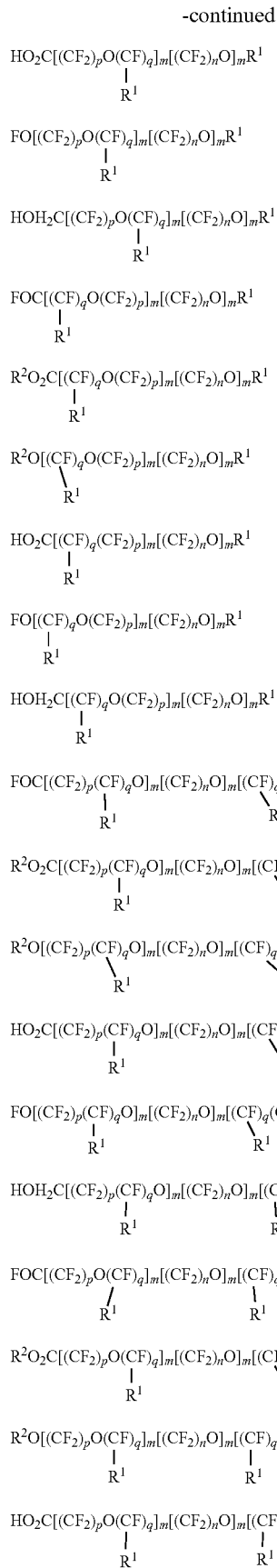

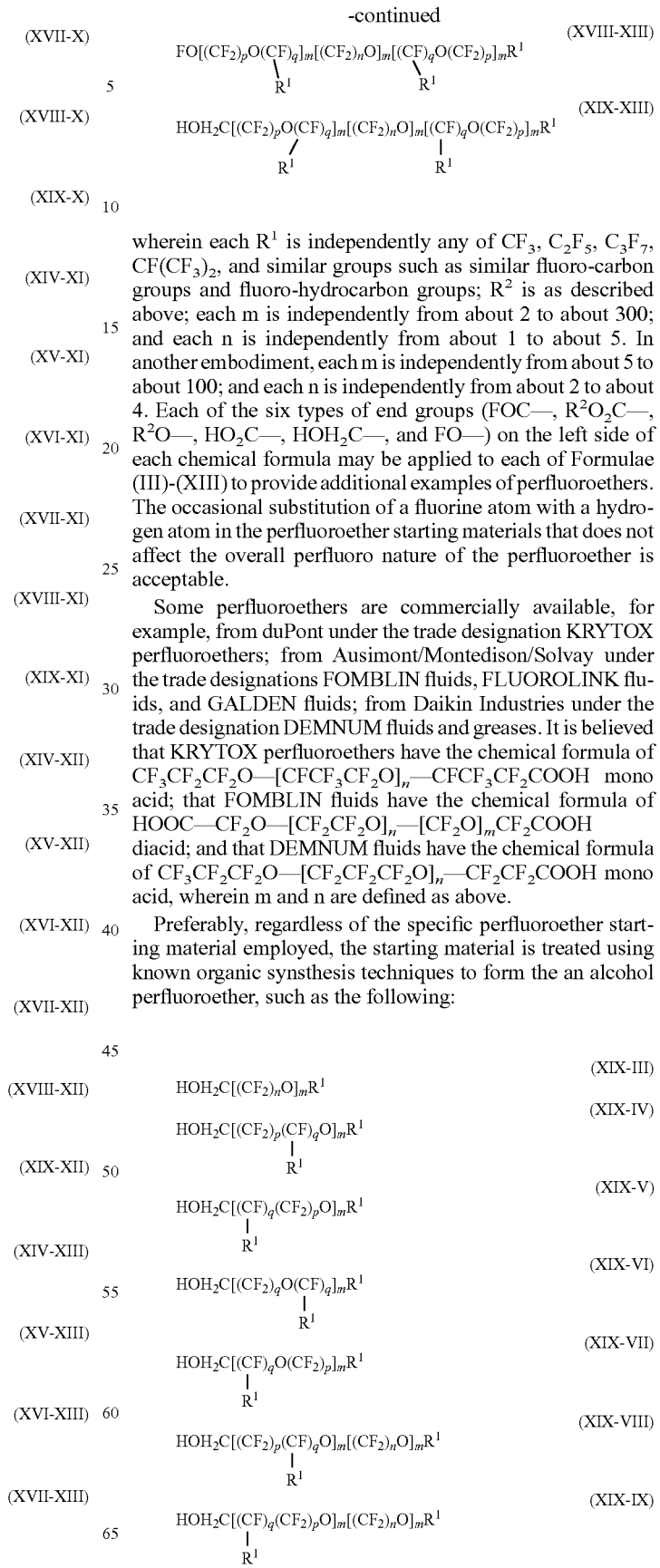

wherein each $R^1$ is independently any of $CF_3$, $C_2F_5$, $C_3F_7$, $CF(CF_3)_2$, and similar groups such as similar fluoro-carbon groups and fluoro-hydrocarbon groups; $R^2$ is as described above; each m is independently from about 2 to about 300; and each n is independently from about 1 to about 5. In another embodiment, each m is independently from about 5 to about 100; and each n is independently from about 2 to about 4. Each of the six types of end groups (FOC—, $R^2O_2C$—, $R^2O$—, $HO_2C$—, $HOH_2C$—, and FO—) on the left side of each chemical formula may be applied to each of Formulae (III)-(XIII) to provide additional examples of perfluoroethers. The occasional substitution of a fluorine atom with a hydrogen atom in the perfluoroether starting materials that does not affect the overall perfluoro nature of the perfluoroether is acceptable.

Some perfluoroethers are commercially available, for example, from duPont under the trade designation KRYTOX perfluoroethers; from Ausimont/Montedison/Solvay under the trade designations FOMBLIN fluids, FLUOROLINK fluids, and GALDEN fluids; from Daikin Industries under the trade designation DEMNUM fluids and greases. It is believed that KRYTOX perfluoroethers have the chemical formula of $CF_3CF_2CF_2O$—$[CFCF_3CF_2O]_n$—$CFCF_3CF_2COOH$ mono acid; that FOMBLIN fluids have the chemical formula of $HOOC$—$CF_2O$—$[CF_2CF_2O]_n$—$[CF_2O]_mCF_2COOH$ diacid; and that DEMNUM fluids have the chemical formula of $CF_3CF_2CF_2O$—$[CF_2CF_2CF_2O]_n$—$CF_2CF_2COOH$ mono acid, wherein m and n are defined as above.

Preferably, regardless of the specific perfluoroether starting material employed, the starting material is treated using known organic synsthesis techniques to form the an alcohol perfluoroether, such as the following:

-continued $$HOH_2C[(CF_2)_pO(CF)_q]_m[(CF_2)_nO]_mR^1 \atop |\atop R^1$$ (XIX-X)

$$HOH_2C[(CF)_qO(CF_2)_p]_m[(CF_2)_nO]_mR^1 \atop |\atop R^1$$ (XIX-XI)

$$HOH_2C[(CF_2)_p(CF)_qO]_m[(CF_2)_nO]_m[(CF)_q(CF_2)_pO]_mR^1 \atop |\quad\quad\quad\quad\quad\quad\quad\quad | \atop R^1 \quad\quad\quad\quad\quad\quad\quad\quad R^1$$ (XIX-XII)

$$HOH_2C[(CF_2)_pO(CF)_q]_m[(CF_2)_nO]_m[(CF)_qO(CF_2)_p]_mR^1 \atop |\quad\quad\quad\quad\quad\quad\quad\quad | \atop R^1 \quad\quad\quad\quad\quad\quad\quad\quad R^1$$ (XIX-XIII)

wherein $R^1$, m, and n are as defined above. Again, it is understood that any of Formulae (III)-(XIII) can treated to provide the corresponding alcohol perfluoroether (the compounds of Formulae (III)-(XIII) having a $CH_2OH$ group on the left side of the formulae).

The perfluoroethers and preferably the alcohol perfluoroethers may be functionalized by combining a given perfluoroether with an alcohol, such as a lower alkyl alcohol (C1-C5) such as methanol, ethanol, isopropanol, propanol, butanol, isobutanol, t-butanol, pentanol, isopentanol, amylalcohol, a metal lower alkyl alcoholate, such as an alkali metal alcoholate such as sodium methylate, sodium ethylate, and sodium isopropylate, or a metal fluoride (alkali metal, alkaline earth metal, or transition metal). When a metal lower alkyl alcoholate is used, the corresponding alcohol is formed (corresponding to the alcoholate) as a byproduct and the resulting functionalized perfluoroether is a metal alcoholate perfluoroether. For example, the metal alcoholate perfluoroether of Formulae (XIX-III)-(XIX-VIII) have the following formula:

$$MOH_2C[(CF_2)_nO]_mR^1$$ (XX-III)

$$MOH_2C[(CF_2)_p(CF)_qO]_mR^1 \atop |\atop R^1$$ (XX-IV)

$$MOH_2C[(CF)_q(CF_2)_pO]_mR^1 \atop |\atop R^1$$ (XX-V)

$$MOH_2C[(CF_2)_pO(CF)_q]_mR^1 \atop |\atop R_1$$ (XX-VI)

$$MOH_2C[(CF)_qO(CF_2)_p]_mR^1 \atop |\atop R^1$$ (XX-VII)

$$MOH_2C[(CF_2)_p(CF)_qO]_m[(CF_2)_nO]_mR^1 \atop |\atop R^1$$ (XX-VIII)

$$MOH_2C[(CF)_q(CF_2)_pO]_m[(CF_2)_nO]_mR^1 \atop |\atop R^1$$ (XX-IX)

$$MOH_2C[(CF_2)_pO(CF)_q]_m[(CF_2)_nO]_mR^1 \atop |\atop R^1$$ (XX-X)

$$MOH_2C[(CF)_qO(CF_2)_p]_m[(CF_2)_nO]_mR^1 \atop |\atop R^1$$ (XX-XI)

$$MOH_2C[(CF_2)_p(CF)_qO]_m[(CF_2)_nO]_m[(CF)_q(CF_2)_pO]_mR^1 \atop |\quad\quad\quad\quad\quad\quad\quad\quad | \atop R^1 \quad\quad\quad\quad\quad\quad\quad\quad R^1$$ (XX-XII)

$$MOH_2C[(CF_2)_pO(CF)_q]_m[(CF_2)_nO]_m[(CF)_qO(CF_2)_p]_mR^1 \atop |\quad\quad\quad\quad\quad\quad\quad\quad | \atop R^1 \quad\quad\quad\quad\quad\quad\quad\quad R^1$$ (XX-XIII)

wherein M is a metal, such as an alkali or alkaline earth metal; $R^1$, m, and n are as defined above. Examples of alkali and alkaline earth metals include lithium, sodium, potassium, ruthenium, cesium, magnesium, calcium, strontium, barium, and the like. Again, it is understood that any of Formulae (III)-(XIII) and their corresponding Formulae (XIV)-(XIX) may be treated to provide the corresponding metal alcoholate perfluoroether (the compounds of Formulae (III)-(XIII) having a $CH_2OM$ group on the left side of the formulae).

The functionalized perfluoroether, such as a metal alcoholate perfluoroether or alcohol perfluoro ether, is contacted with a hydrocarbon containing compound such as an allyl compound or a styrene compound. Hydrocarbylization of the functionalized perfluoroether takes place, which facilitates subsequent attachment of the perfluoroether to a silane compound. For example, an allyl compound may be represented by $$XCHCH=CH_2 \atop |\atop R^4$$ (XXI)

wherein X is a reactive group such as halogen or hydroxy, and $R^4$ is hydrogen, alkyl, hydroxyalkyl, alkoxy, alkyl ether, aryl, aryloxy, substituted aryl, all of which contain from about 1 to about 20 carbon atoms, halogens, hydroxy, and acetoxy.

Some hydrocarbylized perfluoroethers are commercially available, for example, from DuPont under the trade designation KRYTOX allyl ethers. Moreover, the synthesis of such compounds is described in U.S. Pat. No. 6,753,301, which is hereby incorporated by reference. Methods of making and processing allyl ethers is also described in Howell et al, New derivatives of poly-hexafluoropropylene oxide from the corresponding alcohol, *Journal of Fluorine Chemistry*, 126 (2005) 281-288, which is hereby incorporated by reference.

The hydrocarbylized perfluoroether is subject to hydrosilation by contact with a silane compound, preferably in the presence of a catalyst, to form a perfluoropolyether silicon compound. Examples of the silane compounds are represented by Formula (XXII):

$$R_mSiH_n$$ (XXII)

where each R is independently an alkyl, hydroxyalkyl, alkoxy, alkyl ether, aryl, aryloxy, substituted aryl, all of which contain from about 1 to about 20 carbon atoms, halogens, hydroxy, and acetoxy; and m is from about 2 to about 3, n is from 1 to about 2, and m+n equal 4. In another embodiment, each R is independently an alkyl, hydroxyalkyl, alkoxy, alkyl ether, aryl, aryloxy, substituted aryl, all of which contain from about 1 to about 20 carbon atoms; and m is about 3, and n is about 1. In this sense, triorgano silanes can be employed as the silane compound.

Examples of silane compounds include dialkoxyalkyl silanes such as diisopropenoxymethylsilane, dimethoxymethylsilane, diethoxymethylsilane, dipropoxymethylsilane, and dibutoxymethylsilane; trialkoxy silanes such as triisopropenoxysilane trimethoxysilane triethoxysilane tripropoxysilane tributoxysilane; dihalosilanes and trihalosilanes such as trichlorosilane, alkyldichlorosilane. Hundreds of additional examples are not listed for brevity.

Any suitable catalyst can be employed to promote the hydrosilation reaction. Examples of hydrosilation catalysts include platinum containing catalysts such as platinum black, platinum supported on silica, platinum supported on carbon, chloroplatinic acid such as $H_2PtCl_6$, alcohol solutions of chloroplatinic acid, platinum/olefin complexes, platinum/alkenylsiloxane complexes, platinum/beta-diketone complexes, platinum/phosphine complexes and the like; palladium containing catalysts such as palladium on carbon, palladium chloride and the like; nickel containing catalysts; rhodium catalysts, such as rhodium chloride and rhodium chloride/di(n-butyl)sulfide complex and the like; chromium catalysts; other precious metal catalysts, and the like.

The hydrosilation reaction can be carried out using methods known in the art, such as Speier, Homogenous catalysis of hydrosilation by transition metals, Advances in Organometallic Chemistry, vol. 17, pp 407-447, 1979, which is hereby incorporated by reference.

One example of a specific reaction scheme is as follows.

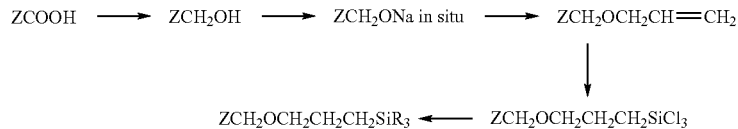

where each R is independently an alkyl, hydroxyalkyl, alkoxy, alkyl ether, aryl, aryloxy, substituted aryl, all of which contain from about 1 to about 20 carbon atoms, halogens, hydroxy, and acetoxy; Z is fluorinated alkyl ether containing from about 2 to about 2,000 carbon atoms.

An advantage associated with the perfluoropolyether silicon compounds is that the methods of making the perfluoropolyether silicon compounds have relatively high yields of final product. In one embodiment, the methods of making the perfluoropolyether silicon compounds have a % yield of about 90% or more. In another embodiment, the methods of making the perfluoropolyether silicon compounds have a % yield of about 95% or more. In yet another embodiment, the methods of making the perfluoropolyether silicon compounds have a % yield of about 97% or more.

Once made, the perfluoropolyether silicon compounds are stored in a container, ampoule, placed in a crucible, or incorporated on and/or into a porous carrier to form a composite that facilitates the coating process. The porous carrier composite may be stored in an air tight or otherwise protected container. The porous carrier may function and/or look like a sponge.

In order to facilitate storing and/or loading the perfluoropolyether silicon compounds to a container, ampoule, crucible, or porous carrier, the perfluoropolyether silicon compounds may be optionally combined with a solvent. It is desirable that the perfluoropolyether silicon compounds are substantially uniformly distributed throughout the porous carrier.

Solvents to which the perfluoropolyether silicon compounds may be combined are generally non-polar organic solvents. Such solvents typically include alcohols such as isopropanol; alkanes such as cyclohexane and methyl cyclohexane; aromatics such as toluene, trifluorotoluene; alkylhaolsilanes, alkyl or fluoralkyl substituted cyclohexanes; ethers; perfluorinated liquids such as perfluorohexanes; and other hydrocarbon containing liquids. Examples of perfluorinated liquids include those under the trade designation Fluorinert™ and Novec™ available from 3M. When combining the perfluoropolyether silicon compounds with one or more solvents, heat may be optionally applied to facilitate formation of a uniform mixture.

A coating catalyst and/or a quencher may be combined with the perfluoropolyether silicon compound or mixture of perfluoropolyether silicon compounds and solvent to facilitate the coating process. Coating catalysts include metal chlorides such as zinc chloride and aluminum chloride, and mineral acids while quenchers include zinc powders and amines. Each is present in the perfluoropolyether silicon compound or mixture of perfluoropolyether silicon compounds and solvent in an amount from about 0.01% to about 1% by weight.

The container, ampoule, crucible, or porous carrier containing the mixture of perfluoropolyether silicon compounds and solvent may be treated to remove the solvent or substantially all of the solvent by any suitable means. For example, evaporation or vacuum distillation may be employed. After solvent is removed, heat is applied until a constant weight is achieved. In this instance, heating at a temperature from about 40 to about 100° C. is useful. In most instances, the perfluoropolyether silicon compounds solidifies, becomes semi-solid, or becomes a low viscosity liquid and is retained in the container, ampoule, crucible, or pores of the porous carrier.

The container, ampoule, crucible, or porous carrier may be made of any material inert to the perfluoropolyether silicon compounds, such as porcelain, glass, pyrex, metals, metal oxides, and ceramics. Specific examples of materials that may form the porous carrier include one or more of alumina, aluminum silicate, aluminum, brass, bronze, chromium, copper, gold, iron, magnesium, nickel, palladium, platinum, silicon carbide, silver, stainless steel, tin, titanium, tungsten, zinc, zirconium, Hastelloy®, Kovar®, Invar, Monel®, Inconel®, and various other alloys.

Examples of porous carriers include those under the trade designation Mott Porous Metal, available from Mott Corporation; those under the trade designation Kellundite available from Filtros Ltd.; and those under the trade designations Metal Foam, Porous Metal Media and Sinterflo®, available from Provair Advanced Materials Inc. methods of using a porous carrier are described in U.S. Pat. No. 6,881,445, which is hereby incorporated by reference.

Coating techniques involve exposing the substrate to the perfluoropolyether silicon compounds in the container, ampoule, crucible, or on the porous carrier in a chamber or closed environment under at least one of reduced pressure, elevated temperature, irradiation, and power. Preferably, reduced pressure and/or elevated temperatures are employed. The reduced pressure, elevated temperatures, irradiation, and/or power imposed induce vaporization or sublimation of the perfluoropolyether silicon compounds into the chamber atmosphere and subsequent self assembly and/or self-polymerization on the substrate surface in a uniform and continuous fashion thereby forming the hydrophobic coating. Alternatively, the substrate is exposed to the perfluoropolyether silicon compounds by dipping, immersing, wipe-on techniques (for example using a cloth), coating using a blade, and the like.

In one embodiment, the substrate is exposed to the perfluoropolyether silicon compounds under a pressure from about 0.000001 to about 760 torr (specifically including no applied vacuum). In another embodiment, the substrate is exposed to the perfluoropolyether silicon compounds under a pressure from about 0.00001 to about 200 torr. In yet another embodiment, the substrate is exposed to the perfluoropolyether silicon compounds under a pressure from about 0.0001 to about 100 torr.

In one embodiment, the perfluoropolyether silicon compounds are heated to a temperature from about 20 to about 400° C. In another embodiment, the perfluoropolyether silicon compounds are heated to a temperature from about 40 to about 350° C. In yet another embodiment, the perfluoropolyether silicon compounds are heated to a temperature from about 50 to about 300° C. Only the perfluoropolyether silicon compounds need to be at the temperature described above to induce coating formation. The substrate is at about the same or at a different temperature as the perfluoropolyether silicon compounds in the chamber. The perfluoropolyether silicon compounds are at about the same or at a different temperature as the atmosphere of the chamber. The substrate is at about the same or at a different temperature as the atmosphere of the chamber. In one embodiment, each of the substrate, perfluoropolyether silicon compounds, and atmosphere is at a temperature from about 20 to about 400° C.

General examples of coating forming techniques include dipping (in a coating solution); wet application (spraying, wiping, printing, stamping); vapor deposition; vacuum deposition; vacuum coating; box coating; sputter coating; vapor deposition or chemical vapor deposition (CVD) such as low pressure chemical vapor deposition (LPCVD), plasma enhanced chemical vapor deposition (PECVD), high temperature chemical vapor deposition (HTCVD); and sputtering. Such techniques are known in the art and not described for brevity sake.

Vapor deposition/chemical vapor deposition techniques and processes have been widely disclosed in literature, for example: *Thin Solid Films*, 1994, 252, 32-37; *Vacuum technology by Ruth A.* $3^{rd}$ edition, Elsevier Publication, 1990, 311-319; *Appl. Phys. Lett.* 1992, 60, 1866-1868; *Polymer Preprints*, 1993, 34,427-428; U.S. Pat. Nos. 6,265,026; 6,171,652; 6,051,321; 5,372,851; and 5,084,302, which are hereby incorporated by reference for their teachings in forming coatings or depositing organic compounds on substrates.

In another embodiment, a thin film can be formed using one or more perfluoropolyether silicon compounds in solution and contacting the substrate surface by immersion or wipe-on with a wet cloth at ambient conditions of the coating solution. Diluting the perfluoropolyether silicon compounds in an inert solvent such as perfluorohexane at a concentration from about 0.001% to about 5% by weight makes the coating solution. The coating solution may alternatively contain from about 0.01% to about 1% by weight of one or more perfluoropolyether silicon compounds. Excess polymer is removed by wiping the surface with a clean tissue paper and then air cured to get the highly cross-linked network of the thin film polymer on the substrate surface.

The perfluoropolyether silicon compounds and/or film formed therefrom has reactive hydroxyl groups, which become involved in chemical bonding (hydrogen and/or covalent) to the substrate. As the substrate surface reacts with moisture (airborne water molecules), making covalent bonds to the surface, similar to self-assembly of layers, thus providing permanent transparent uniform thin coating, which has excellent hydrophobic/oleophobic properties.

The perfluoropolyether silicon compounds, methods and composites of the subject invention are advantageous for providing a thin hydrophobic film or coating on substrates. The perfluoropolyether silicon compounds, methods and composites of the subject invention are also advantageous for providing one or more of the types of films/coating on a substrate: a protective film, an anti-corrosion coating, a wear resistant coating, an anti-smudge film (meaning the substrate surface stays clean).

Substrates include those with porous and non-porous surfaces such as glasses, ceramics, porcelains, fiberglass, metals, and organic materials including thermosets such as polycarbonate, and thermoplastics, and ceramic tile. Additional organic materials include polystyrene and its mixed polymers, polyolefins, in particular polyethylene and polypropylene, polyacrylic compounds, polyvinyl compounds, for example polyvinyl chloride and polyvinyl acetate, polyesters and rubber, and also filaments made of viscose and cellulose ethers, cellulose esters, polyamides, polyurethanes, polyesters, for example polyglycol terephthalates, and polyacrylonitrile.

Glasses specifically include lenses, such as eyewear lenses, microscope slides, decorative glass pieces, plastic sheets, mirror glass, papers, ceramic or marble tile, vehicle/automobile windows, shower doors, building windows and doors, binocular lenses, microscope lenses, telescope lenses, camera lenses, video lenses, televison screens, computer screens, LCDs, mirrors, prisms, and the like.

The coatings formed on the substrate generally have a uniform thickness over the substrate, within that portion of the substrate (the hydrophobic coating is uniformly thick where the hydrophobic coating is formed). In one embodiment, the thickness of the coatings are independently from about 0.1 nm to about 250 nm. In another embodiment, the thickness of the coatings are independently from about 1 nm to about 200 nm. In yet another embodiment, the thickness of the coatings are independently is from about 2 nm to about 100 nm. In still yet another embodiment, the thickness of the coatings are independently from about 5 nm to about 20 nm. In another embodiment, the thickness of the coatings are independently about 10 nm or less. The thickness of the coatings may be controlled by adjusting the deposition parameters.

Another advantage associated with the perfluoropolyether silicon compounds, methods and composites of the subject invention is the environmental benefits provided, since methods of making and using the perfluoropolyether silicon compounds are substantially free of environmental pollution. That is, the methods of making the perfluoropolyether silicon compounds involve reactions that can be performed without a solvent (and/or with small amounts of organic solvents) and hence keep the environment clean by minimizing waste generated thereby.

The following examples illustrate the subject invention. Unless otherwise indicated in the following examples and elsewhere in the specification and claims, all parts and percentages are by weight, all temperatures are in degrees Centigrade, and pressure is at or near atmospheric pressure.

EXAMPLE 1

KRYTOX fluids are commercially available from E. I. du Pont in various molecular weight ranges (600-20000); for example KRYTOX 157FS (L), (M) and (H), was converted into an acid chloride by the treatment with $PCl_5$ followed by reacting with methanol to obtain the corresponding methyl ester. The methyl ester was subjected to reduction into alcohol by sodium borohydride in 2-propanol according to method published in Journal of Fluorine Chemistry 126 (2005) 281-288 by Howell. The preceding alcohol was then taken as the starting material to make the fluorinated organic silicon compound.

To a dry 100 mL three necked round flask was charged 0.9 g (0.036 mol) sodium hydride in a glove box under argon atmosphere and then flask is moved into fume-hood, equipped with stirring bar, thermometer, and a refluxed condenser. 25 g (0.0169 mol) KRYTOX alcohol KDP-4599 average mwt. 1460 and then 50 mL anhydrous THF was added during stirring while continue to keep positive argon atmosphere during the entire course of reaction. This reaction mixture was heated to boil and continue to heat until no more hydrogen gas evolved. After cooling, then 3.2 mL (0.037 mol) of allyl bromide was added slowly into the reaction mixture and allowed to heat for 5 hours. Reaction was cooled and worked up by decomposing it with water. Perfluorohexane/FC-72 a 3M fluorinert solvent is added to separate the organic phase. After washing with water, dried over sodium sulphate and solvent distilled off. Yield (98%) of double bond containing fluorinated organic polymer compound or so called KYTOX allyl ether KDP 4599 with a average molecular weight 1460 amu. This was subjected to IR and NMR to obtain the percent conversion.

Figure 2:
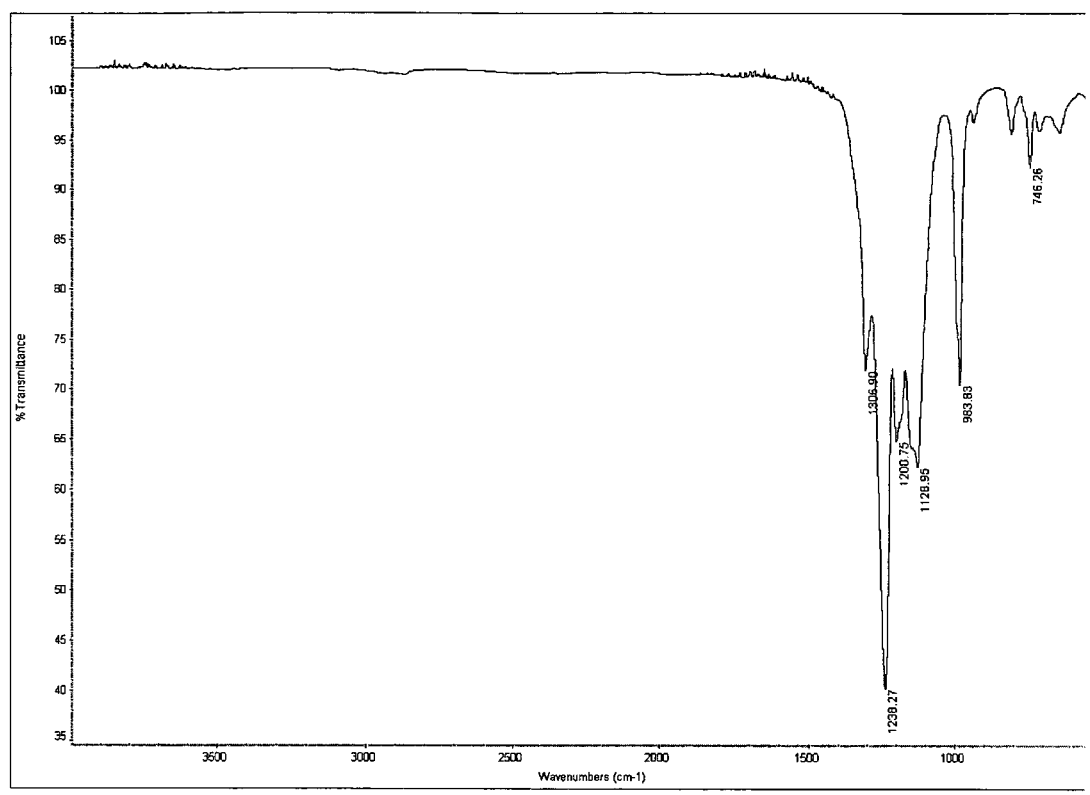
FIG. 2 is an NMR spectrum of an alcohol perfluoroether in accordance with an aspect of the invention.

IR (NaCl, $cm^{-1}$) Vmax: alcohol FIG. 1 and allyl ether FIG. 2.

Figure 3:
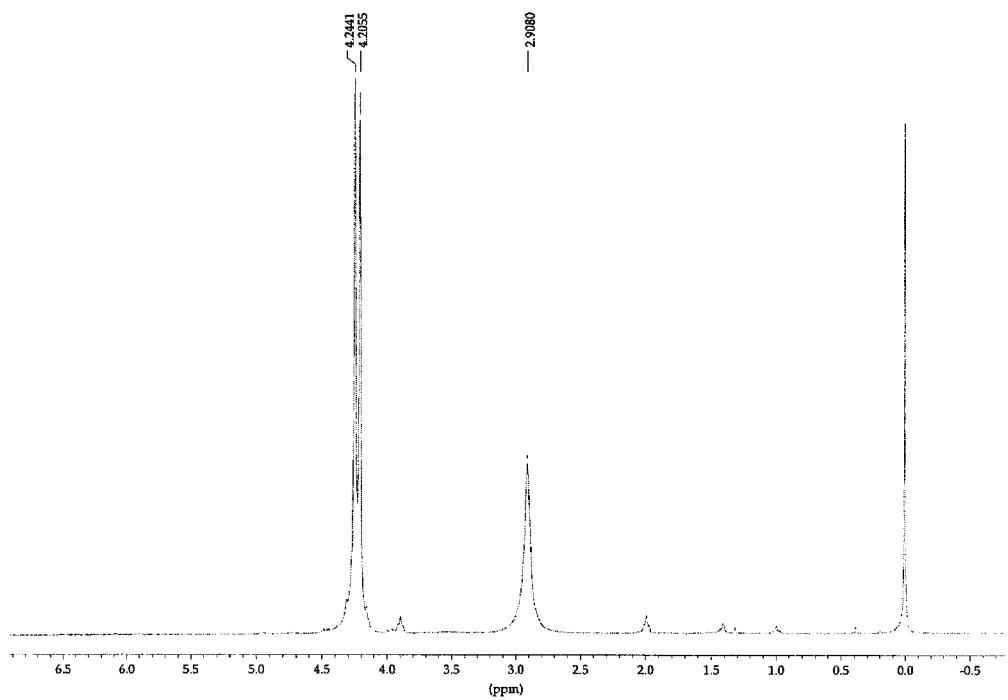
FIG. 3 is an IR spectrum of a hydrocarbylized perfluoroether in accordance with an aspect of the invention.
Figure 4:
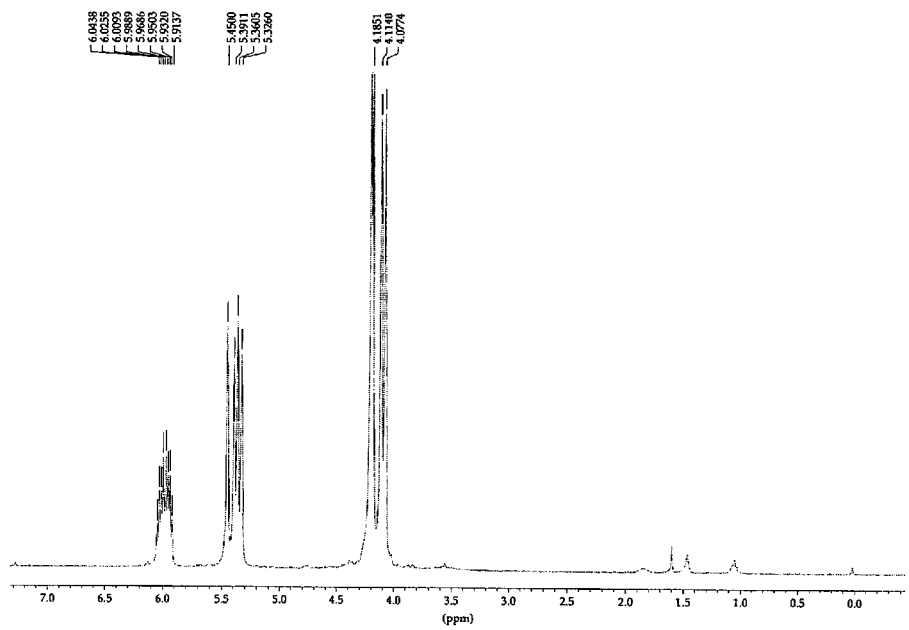
FIG. 4 is an NMR spectrum of a hydrocarbylized perfluoroether in accordance with an aspect of the invention.
Figure 5:
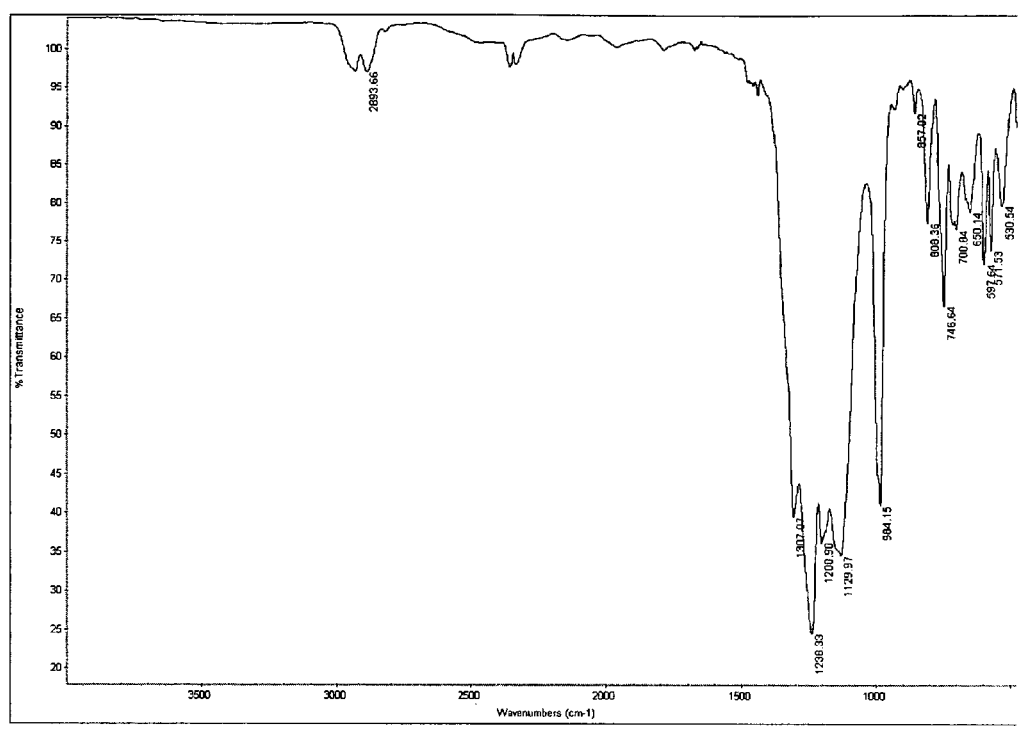
FIG. 5 is an IR spectrum of a perfluoropolyether silicon compound in accordance with an aspect of the invention.
Figure 6:
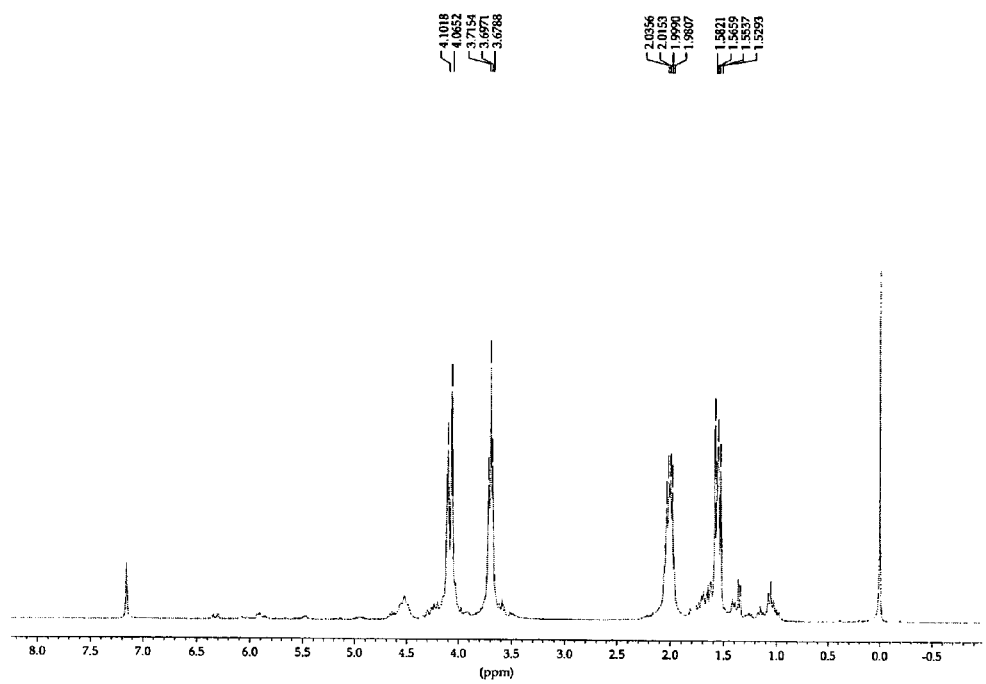
FIG. 6 is an NMR spectrum of a perfluoropolyether silicon compound in accordance with an aspect of the invention.
Figure 7:
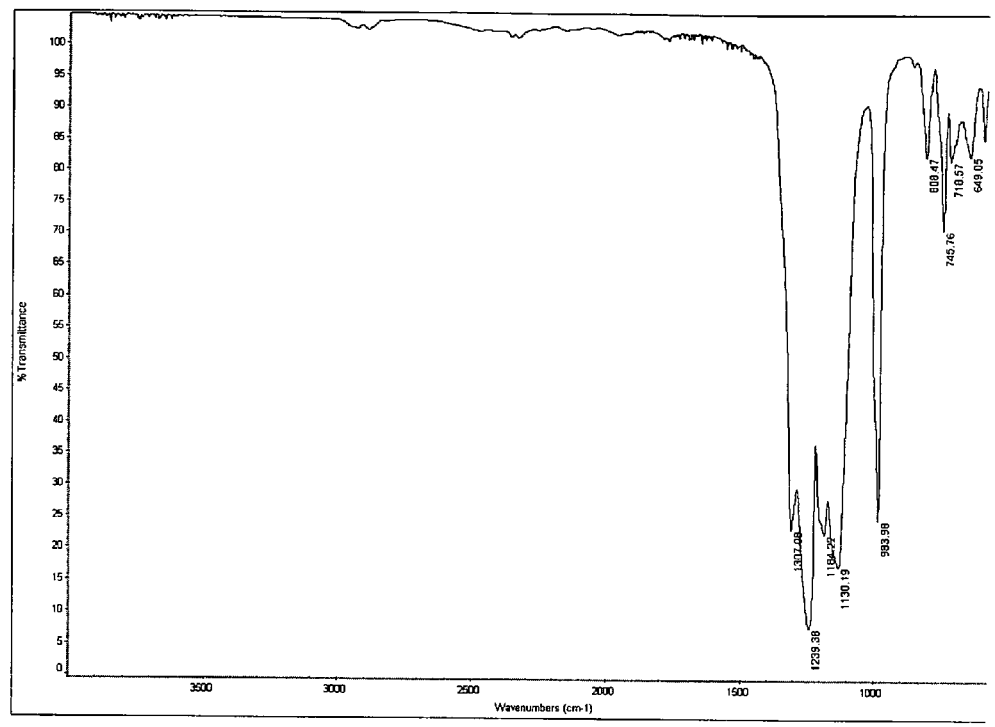
FIG. 7 is an IR spectrum of another perfluoropolyether silicon compound in accordance with an aspect of the invention.
Figure 8:
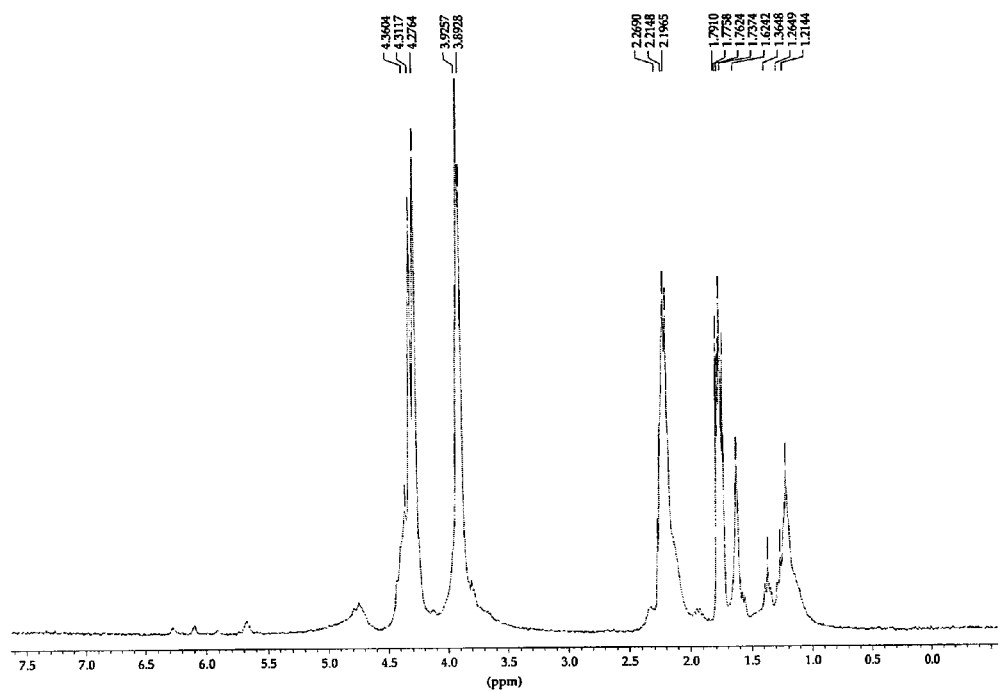
FIG. 8 is an NMR spectrum of another perfluoropolyether silicon compound in accordance with an aspect of the invention.
Figure 9:
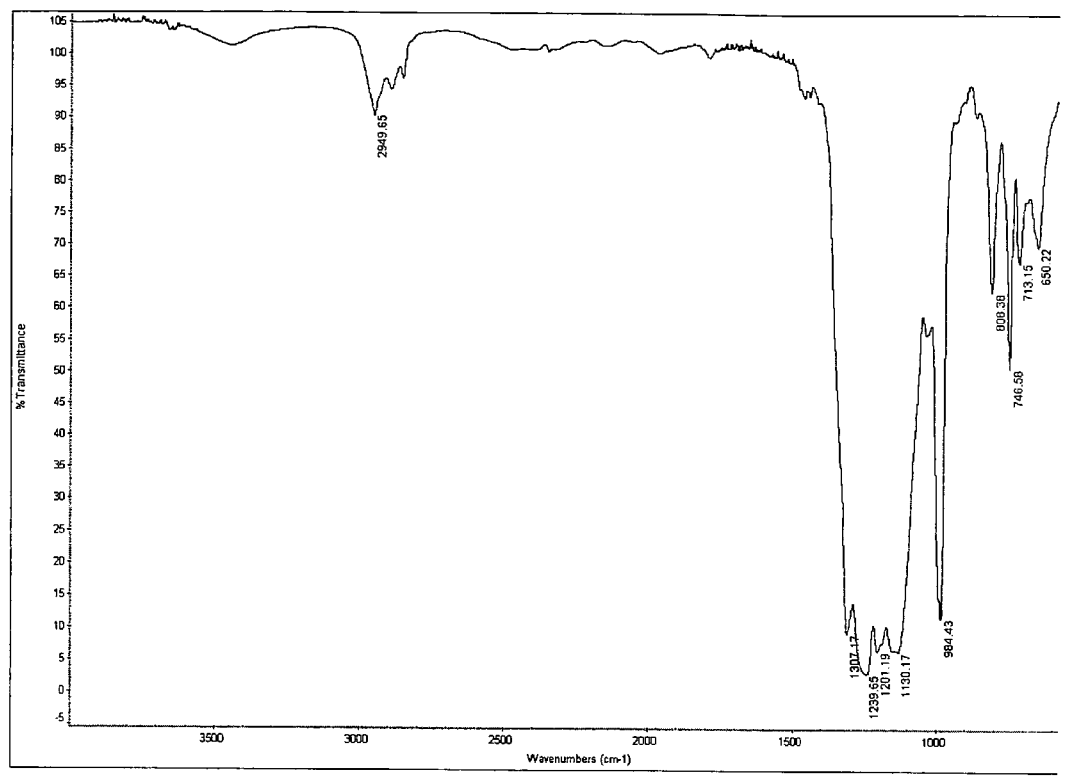
FIG. 9 is an IR spectrum of yet another perfluoropolyether silicon compound in accordance with an aspect of the invention.
Figure 10:
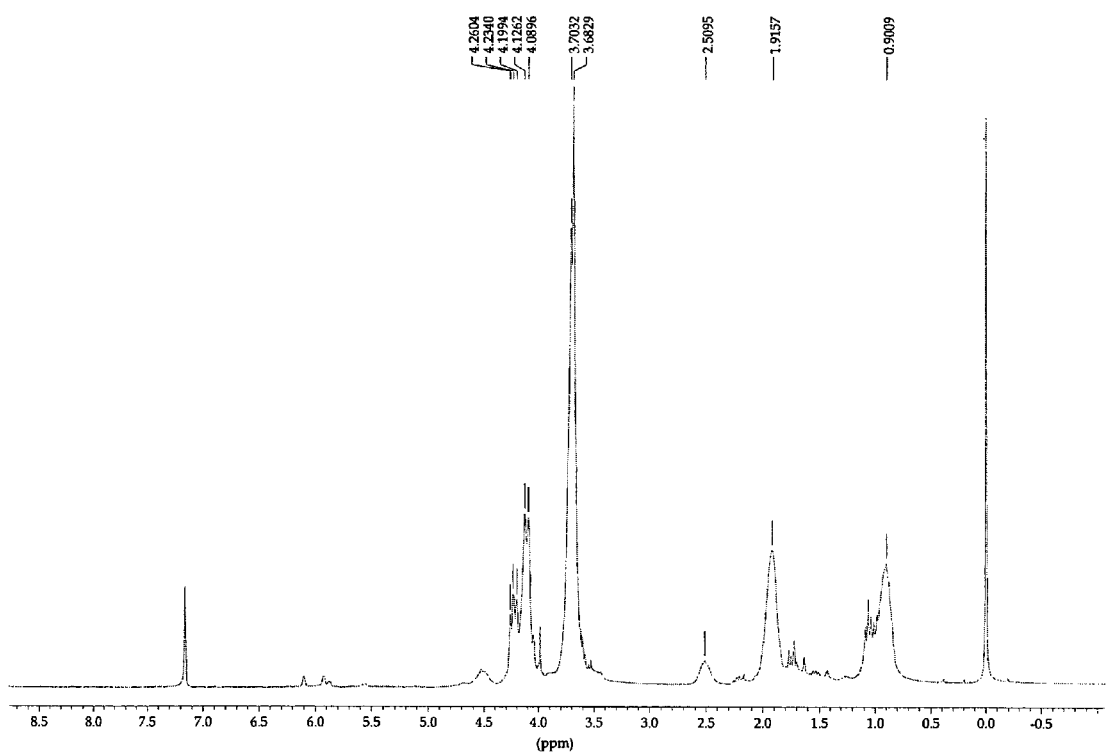
FIG. 10 is an NMR spectrum of yet another perfluoropolyether silicon compound in accordance with an aspect of the invention.
Figure 11:
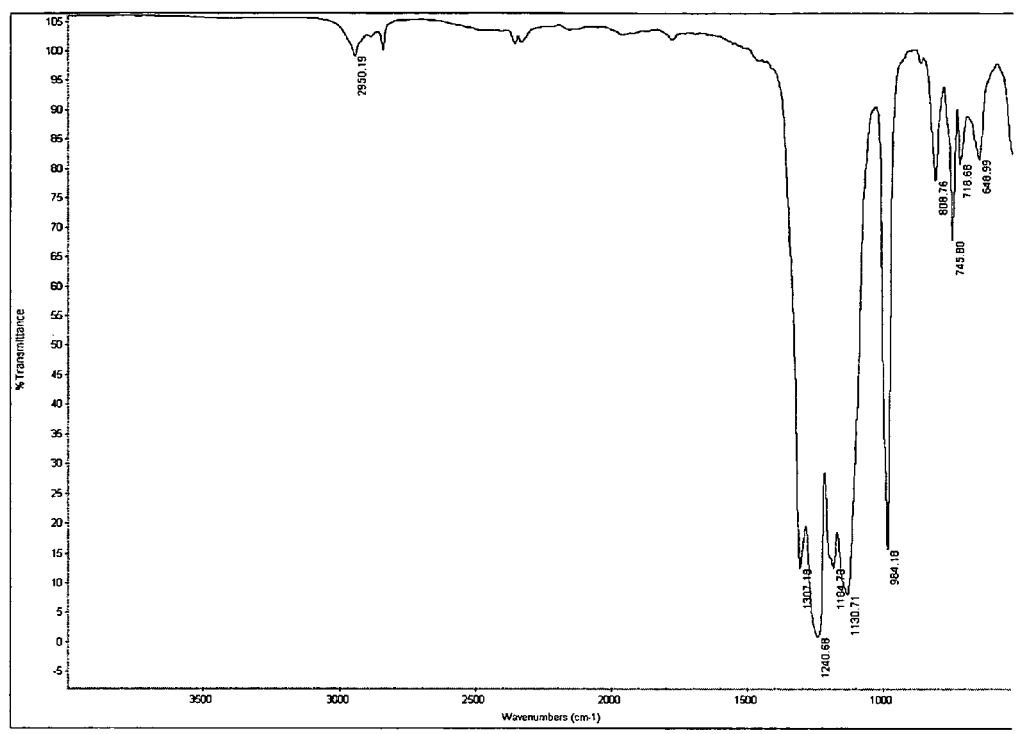
FIG. 11 is an IR spectrum of still yet another perfluoropolyether silicon compound in accordance with an aspect of the invention.
Figure 12:
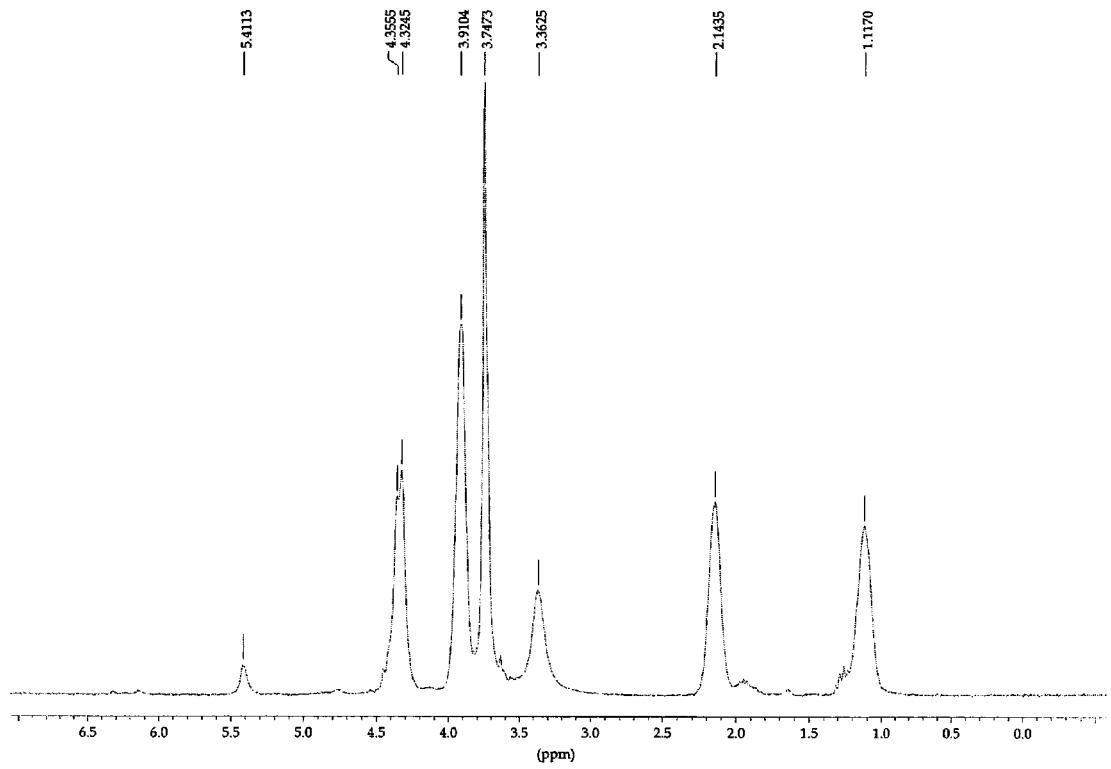
FIG. 12 is an NMR spectrum of still yet another perfluoropolyether silicon compound in accordance with an aspect of the invention.

$^1H$ NMR (300 MHz, $C_6D_6/C_6F_6$): alcohol FIG. 3 and allyl ether FIG. 4.

EXAMPLE 2

Example 1 was repeated except that a commercial di-functional alcohol under trade name FOMBLIN and FLUOROLINK were obtained from Solvay Solexis in various molecular weight range e.g. Zdol-2000, Zdol 4000, FLK D 2000, FLK D 4000, FLK E10H and FLK E all having true functionality or impurity with mono-functionality were treated with sodium hydride same way as Example 1 to converted into corresponding allyl ether.

EXAMPLE 3

Another commercial starting material available from Daikin with a trade name DEMNUM SH can be converted into allyl ether derivative following the same reaction conditions used in Example 1 to give an allyl ether of this class of compound.

EXAMPLE 4

By taking the allyl ether compounds from the above Examples 1, 2, 3 can be subjected into hydrosilation reaction with a specific silane compound.

A pressure reactor vessel was charged with 488 g of KRYTOX allyl ether KDP-4599 ca. mwt. 1465 under nitrogen, 0.8 mL catalyst (0.097 mmol) hydrogen hexachlorolplatinate, and 110 mL trichlorosilane. Reaction vessel was closed under nitrogen and heated for 6 hrs at 165° C. During this time NMR showed no signal for the olefin proton. This was purified by distillation to give pure fluorinated organic silicone material in more than 95% yield.

IR: FIG. 5; NMR: FIG. 6

EXAMPLE 5

Figure 13:
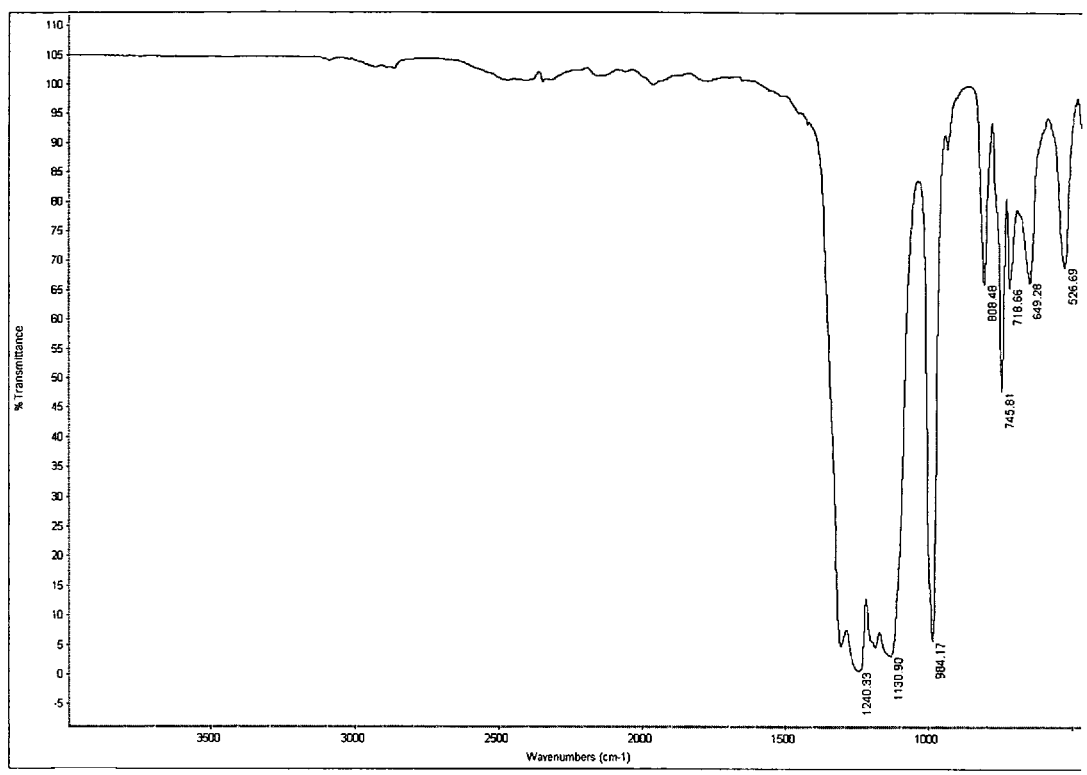
FIG. 13 is an IR spectrum of a hydrocarbylized perfluoroether in accordance with an aspect of the invention.
Figure 14:
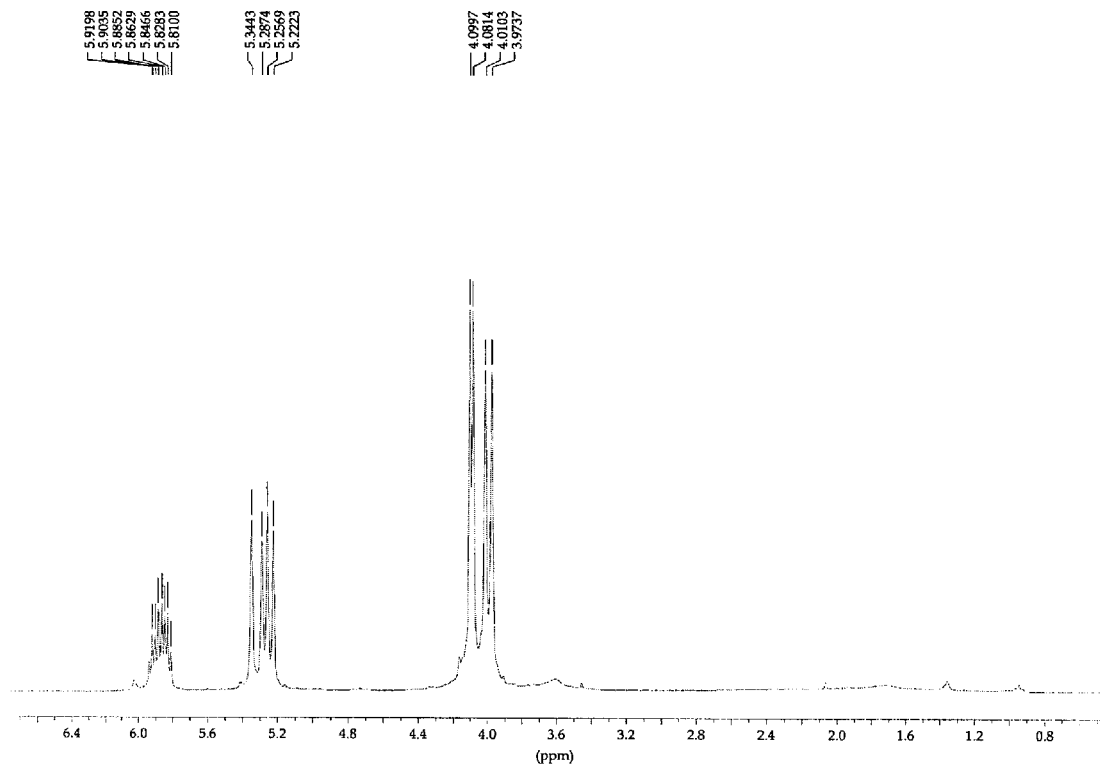
FIG. 14 is an NMR spectrum of a hydrocarbylized perfluoroether in accordance with an aspect of the invention.

A pressure reactor vessel was charged with 75 g of KRYTOX allyl ether KDP-4599 ca. mwt. 4000 (see FIG. 13 for IR and FIG. 14 NMR) under nitrogen, 0.1 mL catalyst (0.012 mmol) hydrogen hexachlorolplatinate, and 22 mL trichlorosilane. Reaction vessel was closed under nitrogen and heated for 8 hrs at 175° C. During this time NMR revealed no signal for the olefin proton. This was purified by distillation to give pure material in more than 95% yield.

IR: FIG. 7; NMR: FIG. 8

EXAMPLE 6

Compound from Example 4 was treated with methanol to convert into trimethoxy fluorinated organic coating material. 60 g material from Example 4, 20 mL anhydrous methanol was added in a flask and heated for one hour under argon. To this was added additional 2 more 20 mL portions of anhydrous methanol at which point no more hydrogen chloride gas evolved. This was washed several times with anhydrous methanol until acid free, which afforded a clear to pale yellow viscous oil. Yield 100%.

IR: FIG. 9; NMR: FIG. 10

EXAMPLE 7

Compound from Example 5 was treated with methanol to convert into trimethoxy fluorinated organic coating material. 12 g material from Example 5, 10 mL anhydrous methanol was added in a flask and heated for one hour under argon. To this was added additional 2 more 20 mL portions of anhydrous methanol at which point no more hydrogen chloride gas evolved. This was washed several times with anhydrous methanol until acid free, which afforded a clear to pale yellow viscous oil. Yield 100%.

IR: FIG. 11; NMR: FIG. 12

EXAMPLE 8

Wet Coating Method

A coating composition was prepared by mixing 0.05-0.1% by weight of the fluorinated organic material prepared in the Example 5 or 6 in perfluorohexane FC-72, FC 77 or HFE 7200 all from 3M in combination with or without iso-propanol. This was tested on bare glass coupons or AR coated lenses, which has last layer of silica and were obtained from Pentax Vision, MN. The coating solution was impregnated in sealed pouch for easy application onto wet wipe cloth. The coating was formed using a dip method of application. Results are summarized in the Table 1.

TABLE 1

| | Contact Angle After | | | | |
|---|---|---|---|---|---|
| 24 hrs | 1 month | 3 months | 5 months | 7 months |
| 110 | 110 | 110 | 110 | 110 |

The coating was formed using a wipe on method of application. Results are summarized in the Table 2.

TABLE 2

| | Contact Angle/Slipperiness Angle After | | | | |
|---|---|---|---|---|---|
| 24 hrs | 1 month | 3 months | 5 months | 7 months |
| 111/8 | 110/8 | 110/8 | 110/8 | 110/8 |

EXAMPLE 9

Polymer from Example 4 was charged onto porous carrier and a glass (lens) substrate coated as described in U.S. Pat. No. 6,881,445. Results are summarized in the Table 3.

TABLE 3

| | No Vacuum | Low vacuum | Low vacuum |
|---|---|---|---|
| Number of lenses | 8 | 50 | 300 |
| Contact angle | 110 | 110 | 110 |

EXAMPLE 10

Polymer from Example 5 was charged onto porous carrier and substrate coated as described in U.S. Pat. No. 6,881,445. Results are summarized in the Table 4.

TABLE 4

| time depo./ Temp °C. | Contact angle of water | Contact angle of olive oil | Abrasion no rub/500 rub | FC-77 wash before/after |
|---|---|---|---|---|
| 5/220 | 100 | 88 | 100/65 | 100/99 |
| 10/220 | 105 | 75 | 105/98 | 105/105 |
| 10/250 | 108 | 75 | 108/100 | 108/108 |
| 10/280 | 110 | 72 | 110/110 | 110/110 |
| 10/300 | 112 | 70 | 112/112 | 112/112 |

COMPARATIVE EXAMPLE 1

Lenses were coated in box coater Satis MC 380H with SATIN pill. Results are summarized in the Table 5.

TABLE 5

| | Thickness value | | | |
|---|---|---|---|---|
| | 5 nm | 7 nm | 10 nm | 12 nm |
| Contact angle | 100 | 105 | 110 | 111 |
| Slip angle | 14 | 11 | 5 | 4.5 |

Lenses were coated with the coating of Example 6 in box coater Satis MC 380H. Results are summarized in the Table 6.

TABLE 6

| | Abrasion | | | | |
|---|---|---|---|---|---|
| Contact angle | 0 | 5000 strk | 10000 strk | 15000 strk | 20000 stoke |
| water | 110 | 110 | 109 | 108 | 105 |
| oil | 72 | 72 | 72 | 72 | 72 |
| Slide angle | 4.5 | 4.5 | 5 | 4.5 | 5 |
| Ink test* | >10 | >10 | >10 | >10 | >10 |

TABLE 6-continued

| | Abrasion | | | | |
|---|---|---|---|---|---|
| Contact angle | 0 | 5000 strk | 10000 strk | 15000 strk | 20000 stoke |
| Surf. tension | 19 | 19 | 19 | 19 | 19 |
| Transmiss. | 100 | 100 | 100 | 100 | 100 |
| Resid. Color | 0 | 0 | 0 | 0 | 0 |

*1 worst, 10 or higher is best

With respect to any figure or numerical range for a given characteristic, a figure or a parameter from one range may be combined with another figure or a parameter from a different range for the same characteristic to generate a numerical range.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of making a compound represented by formula (I):

$$R_mSiH_nR^1OCH_2Z \quad (I)$$

where each R is independently an alkyl, hydroxyalkyl, alkoxy, alkyl ether, aryl, aryloxy, substituted aryl, all of which contain from about 1 to about 20 carbon atoms, halogens, hydroxy, and acetoxy; $R^1$ is an alkyl containing from about 2 to about 10 carbon atoms; Z is fluorinated alkyl ether containing from about 2 to about 2,000 carbon atoms; and m is from about 1 to about 3, n is from 0 to about 2, and m+n equal 3, comprising:
 contacting a hydrocarbylized perfluoroether with a silane compound in the presence of a hydrosilation catalyst to form the compound.

2. The method of claim 1, wherein the hydrocarbylized perfluoroether is made by contacting a functionalized perfluoroether with a hydrocarbon containing compound.

3. The method of claim 2, wherein the functionalized perfluoroether comprises at least one selected from the group consisting of an metal alcoholate perfluoroether and an alcohol perfluoroether and the hydrocarbon containing compound comprises at least one selected from the group consisting of an allyl compound and a styrene compound.

4. The method of claim 2, wherein the functionalized perfluoroether is represented by Formula I:

$$R_mSiH_nR^2OCH_2Z \quad (I)$$

where each R is independently an alkyl, hydroxyalkyl, alkoxy, alkyl ether, aryl, aryloxy, substituted aryl, all of which contain from about 1 to about 20 carbon atoms, halogens, hydroxy, and acetoxy; $R^2$ is an alkyl containing from about 2 to about 10 carbon atoms; Z is fluorinated alkyl ether containing from about 2 to about 2,000 carbon atoms; and m is from about 1 to about 3, n is from 0 to about 2, and m+n equal 3.

5. The method of claim 1, wherein the silane compound is represented by Formula (XXII):

$$R_mSiH_n \quad (XXII)$$

where each R is independently an alkyl, hydroxyalkyl, alkoxy, alkyl ether, aryl, aryloxy, substituted aryl, all of which contain from about 1 to about 20 carbon atoms, halogens, hydroxy, and acetoxy; and m is from about 2 to about 3, n is from 1 to about 2, and m+n equal 4.

6. The method of claim 1, wherein the silane compound is at least one selected from the group consisting of dialkoxyalkyl silanes, trialkoxy silanes, dihalosilanes, and trihalosilanes.

7. The method of claim 1, wherein the hydrosilation catalyst comprises at least one selected from the group consisting of the platinum containing catalysts, palladium containing catalysts, nickel containing catalysts, rhodium catalysts, and chromium catalysts.

8. A method of making a compound represented by formula (I):

$$R_mSiH_nR^1OCH_2Z \qquad (I)$$

where each R is independently an alkyl, hydroxyalkyl, alkoxy, alkyl ether, aryl, aryloxy, substituted aryl, all of which contain from about 1 to about 20 carbon atoms, halogens, hydroxy, and acetoxy; $R^1$ is a propylene group: Z is fluorinated alkyl ether containing from about 2 to about 2,000 carbon atoms; and m is from about 1 to about 3, n is from 0 to about 2, and m+n equal 3, comprising:

contacting a hydrocarbylized perfluoroether with a silane compound in the presence of a hydrosilation catalyst to form the compound.

9. The method of claim 8, wherein the hydrocarbylized perfluoroether is made by contacting a functionalized perfluoroether with a hydrocarbon containing compound.

10. The method of claim 9, wherein the functionalized perfluoroether comprises at least one selected from the group consisting of an metal alcoholate perfluoroether and an alcohol perfluoroether and the hydrocarbon containing compound comprises at least one selected from the group consisting of an allyl compound and a styrene compound.

11. The method of claim 9, wherein the functionalized perfluoroether is made from a perfluoroether having an end group comprising at least one selected from the group consisting of FOC—, $R^2O_2C$—, $R^2O$—, $HO_2C$—, $HOH_2C$—, and FO—, where $R^2$ is alkyl containing from about 2 to about 10 carbon atoms.

12. The method of claim 8, wherein the silane compound is represented by Formula (XXII):

$$R_mSiH_n \qquad (XXII)$$

where each R is independently an alkyl, hydroxyalkyl, alkoxy, alkyl ether, aryl, aryloxy, substituted aryl, all of which contain from about 1 to about 20 carbon atoms, halogens, hydroxy, and acetoxy; and m is from about 2 to about 3, n is from 1 to about 2, and m+n equal 4.

13. The method of claim 8, wherein the silane compound is at least one selected from the group consisting of dialkoxyalkyl silanes, trialkoxy silanes, dihalosilanes, and trihalosilanes.

14. The method of claim 8, wherein the hydrosilation catalyst comprises at least one selected from the group consisting of the platinum containing catalysts, palladium containing catalysts, nickel containing catalysts, rhodium catalysts, and chromium catalysts.

15. A method of making a compound represented by formula:

$$R_mSiH_nR^1OCH_2Z \qquad (I)$$

where each R is independently an alkyl, hydroxyalkyl, alkoxy, alkyl ether, aryl, aryloxy, substituted aryl, all of which contain from about 1 to about 20 carbon atoms, halogens, hydroxy, and acetoxy; $R^1$ is an alkyl containing from about 2 to about 5 carbon atoms; Z is fluorinated alkyl ether containing from about 2 to about 2,000 carbon atoms; and m is from about 2 to about 3, n is from 0 to about 1, and m+n equal 3, comprising:

contacting a hydrocarbylized perfluoroether with a silane compound in the presence of a hydrosilation catalyst to form the compound.

16. The method of claim 15, wherein the hydrocarbylized perfluoroether is made by contacting a functionalized perfluoroether with a hydrocarbon containing compound.

17. The method of claim 16, wherein the functionalized perfluoroether comprises at least one selected from the group consisting of an metal alcoholate perfluoroether and an alcohol perfluoroether and the hydrocarbon containing compound comprises at least one selected from the group consisting of an allyl compound and a styrene compound.

18. The method of claim 16, wherein the functionalized perfluoroether is made from a perfluoroether having an end group comprising at least one selected from the group consisting of FOC—, $R^2O_2C$—, $R^2O$—, $HO_2C$—, $HOH_2C$—, and FO—, where $R^2$ is alkyl containing from about 2 to about 10 carbon atoms.

19. The method of claim 15, wherein the silane compound is represented by Formula (XXII):

$$R_mSiH_n \qquad (XXII)$$

where each R is independently an alkyl, hydroxyalkyl, alkoxy, alkyl ether, aryl, aryloxy, substituted aryl, all of which contain from about 1 to about 20 carbon atoms, halogens, hydroxy, and acetoxy; and m is from about 2 to about 3, n is from 1 to about 2, and m+n equal 4.

20. The method of claim 15, wherein the silane compound is at least one selected from the group consisting of dialkoxyalkyl silanes, trialkoxy silanes, dihalosilanes, and trihalosilanes.

* * * * *